United States Patent [19]

Hughes

[11] Patent Number: 4,840,619

[45] Date of Patent: Jun. 20, 1989

[54] SYRINGE

[76] Inventor: Elaine L. Hughes, 3009 Castle Dr., Blue Springs, Mo. 64015

[21] Appl. No.: 199,323

[22] Filed: May 26, 1988

[51] Int. Cl.⁴ ............................................. A61M 5/00
[52] U.S. Cl. .................................. 604/187; 604/192; 604/198
[58] Field of Search ............... 604/240, 241, 242, 243, 604/198, 195, 194, 187, 192

[56] References Cited

U.S. PATENT DOCUMENTS

| | | | |
|---|---|---|---|
| 2,875,760 | 3/1959 | Haber | 604/242 |
| 3,648,695 | 3/1972 | Bowen | 604/243 X |
| 4,237,882 | 12/1980 | Wickham . | |
| 4,425,120 | 1/1984 | Sampson et al. . | |
| 4,500,312 | 2/1985 | McFarlane . | |
| 4,573,976 | 3/1986 | Sampson et al. . | |
| 4,596,562 | 6/1986 | Vernon . | |
| 4,610,667 | 9/1986 | Pedicano et al. . | |
| 4,631,057 | 12/1986 | Mitchell . | |
| 4,643,200 | 2/1987 | Jennings, Jr. . | |
| 4,655,751 | 4/1987 | Harbaugh . | |
| 4,664,654 | 5/1987 | Strauss . | |
| 4,666,435 | 5/1987 | Braginetz . | |
| 4,681,567 | 7/1987 | Masters et al. . | |
| 4,693,708 | 9/1987 | Wanderer et al. . | |
| 4,695,274 | 9/1987 | Fox . | |
| 4,740,205 | 4/1988 | Seltzer et al. | 604/241 X |

Primary Examiner—John D. Yasko
Attorney, Agent, or Firm—Litman McMahon & Brown

[57] ABSTRACT

An improved syringe for administering injections includes a syringe barrel with an interior chamber, a reciprocating plunger within the chamber, a needle flow communicating with one end of the chamber and a mechanism for removing the needle by remote manipulation by the administrator of an injection without directly touching the needle. The mechanism includes a projection extending radially outward from the needle that is selectively engageable by a projection receiving slot on a sleeve mounted over the barrel. The sleeve loosely fits on the barrel so as to be slidable and rotatable and includes a first configuration wherein the sleeve does not engage the needle, a second configuration wherein the slot engages the projection to allow a user to rotate and disengage the needle and a third configuration wherein the sleeve extends over the needle to protect a user from being accidentally stuck by the needle after use.

10 Claims, 1 Drawing Sheet

U.S. Patent  Jun. 20, 1989  4,840,619
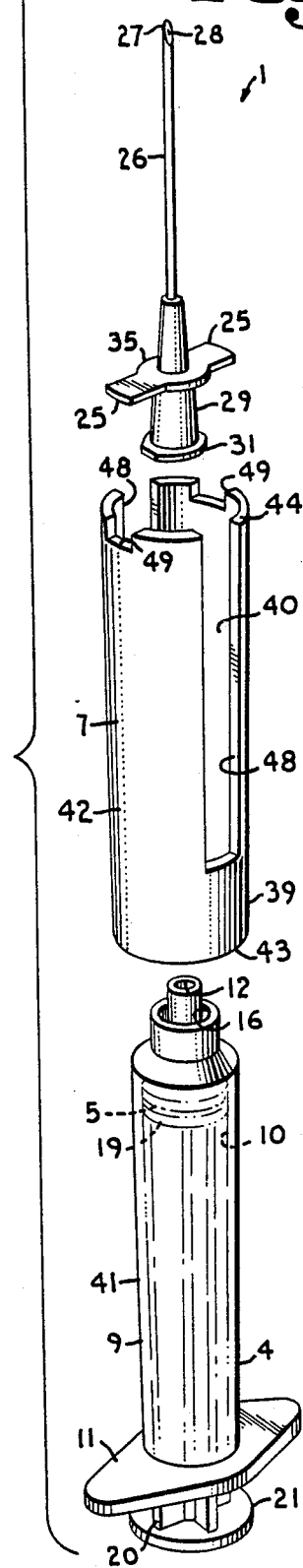
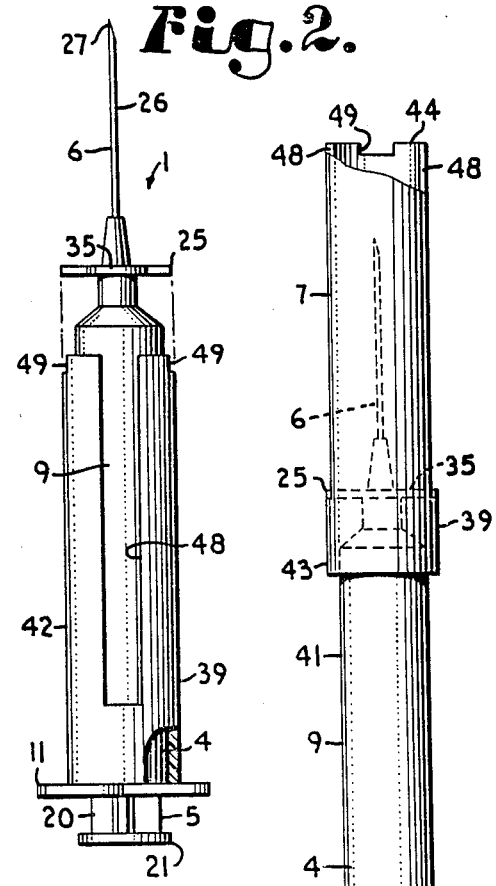
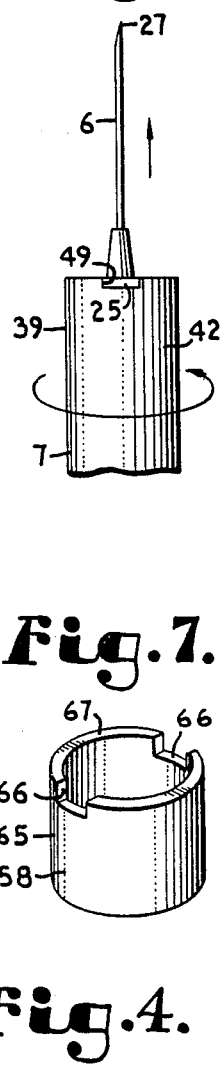
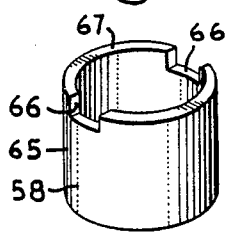
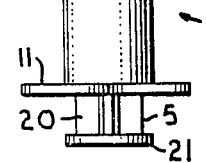
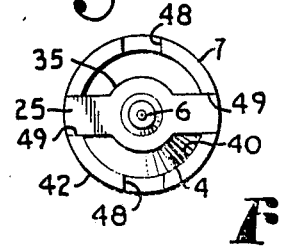
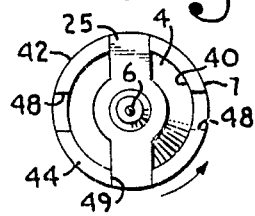
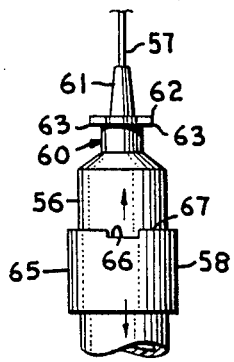

SYRINGE

BACKGROUND OF THE INVENTION

The present invention relates to syringes of the type utilized to penetrate the skin or another membrane of a human and, in particular, to syringes which provide protection to a second person from accidental puncture by the syringe after it has been utilized with to inject the first person.

Medical personnel who are responsible for administering injections, taking blood samples or any of the other medical procedures which require penetration of the human body by a needle or similar device, have always faced a risk of accidental puncture of their own skin by the needle after they have utilized it in a patient. There have always been needle transferrable type diseases which may be transferred from a patient to the medical practitioner by such accidental puncture or strike of the practitioner subsequent to use of the needle in the patient.

Historically, one of the most common diseases transferred has been serum hepatitis. Although hepatitis can be a very dangerous disease, most practitioners have usually attempted to prevent the onset of hepatitis, when accidentally stuck by a needle, by taking a immunoglobulin injection and, if the disease did set into the practitioner, its effects could be treated such that it was seldom deadly. However, the advent and subsequent spread of acquired immune deficiency syndrome (AIDS) has made the potential puncture of the practitioner's skin by an AIDS carrying needle a deadly event.

Numerous devices have been recently developed to cover the needle after an injection and thereby protect the practitioner from accidental puncture by the needle. While these devices are suitable for protecting the needle while it is maintained on the syringe, the protection provided by this type of shield fails when the needle must be removed.

In particular, most hospitals and similar institutions have a policy of removing the contaminated needle from the syringes such that they can be disposed of separately. The needles are normally placed in a collection receptacle such as a box located at a central location in a hospital ward and each of the needles must be removed by a nurse or related health care practitioner. Because the needles must be twisted as they are removed and the practitioner must have a fairly good grip of the neck or base of the needle, the practitioner often slips during the removal process leading to punctures. Consequently, it is desirable for a practitioner to be able to remove the needle from the remainder of the syringe without the practitioner having to directly grasp the needle itself or the base of the needle in order to rotate it.

Several prior art devices have been developed which have attempted to resolve this problem. In particular, in the U.S. Pat. to Wickham No. 4,237,882 is disclosed a funnel-shaped device to receive the needle from the syringe after usage and to remove the needle for eventual storage therein. The funnel of this device provides a wide target for the practitioner such that it is unlikely that the practitioner would stick themself during placement of the needle within the funnel. The major disadvantage with this device is that it is relatively quite large. As it is desirable for the needles to be stored in as small a volume as possible, since they require special handling, the large volume of the device shown in this patent complicates disposal rather than simplifies it.

Another structure for removing the needle is shown in U.S. Pat. to Pedicano et al. No. 4,610,667 wherein a sleeve is normally carried in surrounding relationship to the barrel of the syringe but is completely removable from the syringe. In the end of the sleeve is a tool that can be positioned over the needle, when the sleeve is reversed, and, in particular, over the base of the needle such that the needle can be rotated and removed from the syringe. The major problem with this device is that the practitioner is exposed to a high chance of receiving a puncture wound from the needle when the sleeve is placed over the needle and the risk is not greatly reduced as compared to simply placing a cap over the needle.

Further concerns with the syringe of this type are that the practitioner is provided with some protection during transportation of the needle from the location where an injection is made to the location whereat the needle is removed from the remainder of the syringe. Consequently, it is desirable to have an apparatus that allows both remote removal of the needle or alternatively protection against puncture while the needle is carried. It is also preferable that the needle removing apparatus while allowing removal of the needle without actually touching the needle or the base of the needle also allow the practitioner to firmly grasp the syringe during usage.

OBJECTS OF THE INVENTION

Therefore, the objects of the present invention are: to provide a syringe having a needle with a protective device which allows a practitioner to remove the needle from the syringe without having to touch the needle or the base of the needle and without having to insert the needle into a receptacle thereby avoiding the potential of puncture by contaminated needle; to provide such a syringe having a needle with radially outward extending ears and wherein the device includes a sleeve slidably located on a barrel associated with the syringe and with the sleeve having ear engaging slots at an end thereof closest the needle such that when the sleeve is slid along the barrel of the syringe toward the needle, the slots engage the ears to allow rotation and dislodgement of the needle by rotation of the sleeve by the practitioner; to provide such a syringe wherein the sleeve includes a second pair of deeper slots which allow the sleeve to be extended out over the needle in protective relationship thereto such that a practitioner may carry the syringe with the sleeve held in such a protective position to prevent accidental puncture to the practitioner while walking with the syringe; to provide such a syringe which allows the practitioner to firmly grasp the barrel of the syringe during usage; and to provide such a syringe which is relatively inexpensive to manufacture, easy to use and particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a partially exploded perspective view of a syringe in accordance with the present invention including a syringe body having a barrel, a protective and needle dislodging sleeve and a needle with a base for attaching the needle to the body.

FIG. 2 is a side elevational view of the syringe with the sleeve thereof in a retracted position and with portions thereof broken away to show detail.

FIG. 3 is a fragmentary side elevational view of the syringe showing the sleeve in a needle disengaging position and illustrating rotation of the sleeve to disengage the needle.

FIG. 4 is a side elevational view of the syringe with the sleeve in a protective configuration thereof and showing the needle in phantom lines.

FIG. 5 is a front elevational view of the syringe with the sleeve in the protective configuration thereof.

FIG. 6 is a front elevational view of the syringe with the sleeve in a needle dislodging configuration thereof, as shown in FIG. 3.

FIG. 7 is a perspective view of a first modified sleeve in accordance with the present invention.

FIG. 8 is a side elevational view of the first modified sleeve mounted on an associated syringe.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Illustrated in FIGS. 1 through 6 is a first embodiment of an apparatus for medically penetrating the skin of a patient in order to deliver drugs, remove blood samples or the like and in the present embodiment the illustrated apparatus is a hypodermic syringe generally designated by the reference numeral 1. The syringe 1 includes a body 4, a plunger 5, a needle 6 and a needle removing means or mechanism 7.

The body 4 and plunger 5 of the illustrated syringe 1 are conventional. In particular, the body 4 includes a barrel or barrel portion 9 with an internal cylindrically shaped cavity 10 within which the plunger 5 is slidably received to allow reciprocation of the plunger 5 relative to the cavity 10. The body 4 includes tabs 11 radially extending outward from one end thereof positioned to facilitate gripping by a user. At an end of the body 4 opposite the tabs 11 and coaxially aligned with the internal chamber 10 is a discharge aperture 12. Surrounding the discharge aperture 12 is a first half of a locking mechanism 16 of the type conventionally referred to as a leur lock. The lock mechanism 16 is coaxially aligned with the aperture 12 and is of the twist or rotate to connect and disconnect type.

The plunger 5 includes a head 19, a shaft 20 and an operator depressing pad 21. The head 19 is positioned at one end of the plunger 5 and is sealably and slidably received within the body internal chamber 10 such that, when the plunger 5 is depressed, fluid within the internal chamber 10 between the plunger head 19 and the aperture 12 is expelled through and from the aperture 12. The shaft 20 is connected to the head 19 and extends outward from the internal chamber 10. Attached to the shaft 20 opposite the head 19 is the pad 21 which allows a user thereof to push against the plunger 4 while holding the body tabs 11 and the barrel portion 9 of the body 4.

The needle 6 is similar to conventional needles except for the addition of engaging means, such as a projection or illustrated ears 25 for cooperating with the needle removing mechanism 7. In particular, the needle 6 includes an elongate hollow shaft 26 ending at one end thereof in a sharp point 27 and having an internal lumen opening outwardly at an aperture 28 near the point 27. Opposite the needle point 27 is a connecting base 29. The connecting base includes a second half of a lock mechanism 31 designed to cooperate with and securely lock to the first half of the lock mechanism 16 on the syringe body 4. The lock mechanism 31 is generally positioned so that the needle shaft 26 and the internal lumen associated with the needle shaft 26 are coaxially aligned with the body internal chamber 10. When the needle 6 is positioned such that the lock mechanisms 16 and 31 are secured together, fluid from the internal chamber 10 may be selectively urged by a user of the syringe 1 through the aperture 12, the needle shaft 26 and out the aperture 28 when a user depresses the plunger 5.

The ears 25 are fixedly secured to the needle connecting base 29 and extend radially outward therefrom. It is important that the ears 25 extend sufficiently outward to engage the needle removing mechanism 7 as will be discussed below. In the illustrated embodiment, the ears 25 are oppositely directed halves of a relatively flat plate 35 which is generally aligned to be perpendicular to the central axis of the needle shaft 26 and which is fixedly attached to the base 29.

The needle removing mechanism 7 of the present embodiment comprises a sleeve 39 slidably received around the syringe body 4. The sleeve 39 has an interior surface 40 which slides along and rotates relative to an exterior surface 41 of the body. The sleeve 39 also has an exterior surface 42 adapted to be gripped by a user of the syringe 1. When the syringe 1 is assembled for use, the sleeve 39 cannot be removed from the syringe without first moving the needle 6 because of interference from the body tabs 11 and needle ears 25 preventing the sleeve 39 from sliding completely therepast.

The sleeve 39 has first and second opposite ends 43 and 44. When mounted on the syringe body 4, the sleeve end 43 is closer to the body tabs 11 than the opposite and needle engaging end 44. The sleeve 39 has a first operative configuration, as seen in FIG. 2, wherein the sleeve end 43 generally abuts against the body tabs 11. This first configuration is a non-needle removing or protecting configuration. The sleeve 39 has a second configuration, as seen in FIG. 4, wherein the sleeve end 44 is substantially spaced from the tabs 11 and the sleeve 39 is in a needle protecting configuration. The sleeve 39 also has a third configuration, as seen in FIGS. 3 and 6 wherein the sleeve 39 is in a needle 6 removing configuration.

The sleeve 39 has a first set of elongate "deep" slots which extend nearly the entire length of the sleeve 39 from the sleeve end 44. The slots 48 pass entirely through the side or wall of the sleeve 39 and are aligned to be generally parallel to the axis of the sleeve 39. The slots 49 are sized to be sufficiently wide to allow the ears 25 of the needle 6 to be slidably received therein. In this manner, the sleeve 39, when appropriately aligned, can be slid along the body 4 such that the ears 25 pass into and along respective slots 48 until the sleeve 39 is in the position shown in FIG. 4. In this position, the needle 6 is completely surrounded by the sleeve 39 and cannot accidentally puncture a user thereof.

A second set of "shallow" slots 49 also extend along the sleeve 39 from the sleeve end 44 parallel to the axis of the sleeve 39. The slots 49 are so positioned and sized so as to readily receive the ears 25 when the sleeve 39 is rotated such that the ears 25 align with the slots 49. The slots 49 are not as long as the slots 48. In this manner, when a user wishes to remove a needle 6 from the syringe 1, the slots 49 are engaged with the ears 25 and the sleeve 39 is rotated such that the needle 6 is also consequently rotated by action of the ears 25 acting thereon. The lock mechanisms 16 and 31 are thereby unlocked and the needle 6 is subsequently pushed outward by the sleeve 39 such that it is removed from the remainder of the syringe 1. This is preferably accomplished over a disposal location for the needle 6 so that the needle 6 falls into a receptacle therefor.

It is foreseen that the long slots 48 could also be used for the purpose of removing the needle 6.

In use, the user assembles the syringe 1 in the fashion shown in FIG. 2. Where an injection is to be given to a patient, the syringe 1 is filled with the fluid to be injected by withdrawing the plunger 4 at such a time when the needle 6 is immersed in the fluid to be injected. The fluid is then drawn into the body chamber 10 through the needle shaft 26. The user then penetrates the skin of the patient with the needle point 26 such that the needle aperture 28 is positioned subdermally in the patient. The injection is then administered and the needle 6 withdrawn from the patient.

If the user must travel to a location where the needle 6 is to be discarded, the sleeve 39 is positioned so that the ears 25 are received by the slots 48 and the sleeve is extended over the needle 6 so that the sleeve 39 is in the needle protecting configuration thereof, as shown in FIG. 4. When the user is ready to discard the needle 6, the slots 49 are positioned, such as is shown in FIGS. 3 and 6, so as to engage the ears 25. The sleeve 39 is then twisted or rotated about the axis thereof so as to rotate the ears 25 and subsequently the needle 6 such that the lock mechanisms 16 and 31 disengage and the needle 6 is then pushed axially outward to disconnect same from the remainder of the syringe 1. The sleeve 39 is tilted downwardly such that the needle 6 then falls free from the sleeve 39. It is noted that the slot 48 in the sleeve also allows a user to directly grip the syringe body 4 during administration of the injection to improve the grip thereon.

Shown in FIGS. 7 and 8 is an alternative embodiment of a syringe in accordance with the present invention, generally designated by the reference numeral 55. The syringe 55 is quite similar to the syringe 1 of the previous embodiment and, therefore, an extensive reiteration of the syringe 55 is not necessary.

In particular, the syringe 55 includes a body 56, a needle 57 and a needle removing mechanism 58. The syringe body 56 is an elongate tube which receives fluid therein and which communicates such fluid with the needle 57 for distribution to a patient or which allows withdrawal of such fluid from a patient. The needle 57 is connected to the body 56 by a twist connecting mechanism 60 requiring rotation of the needle relative to the body 56 about a common axis thereof. The connecting mechanism 60 allows the needle 57 to be placed on the body 56 or to be removed therefrom if properly twisted.

The needle 57 includes a base 61 having a radial projection 62 extending outwardly therefrom. The illustrated projection includes a pair of ears 63.

The needle removing mechanism 58 includes a sleeve 65 which is slidably received on the syringe body 56. The sleeve 65 includes a set of slots 66 which are circumferentially spaced around an end 67 thereof so as to be slidably engageable with the ears 62 and 63. In this manner, as with the sleeve 39 of the previous embodiment, the sleeve 65 can be slid along the body 56 by a user thereof such that the slot 66 engages and receives the ears 62 and 63 and, subsequently, the sleeve 65 is rotated such that the ears 62 and 63 transfer the rotation to the needle 57 and subsequently to the twist connecting mechanism 60 such that the twist connecting mechanism 60 is disconnected into two portions thereof. Thereafter, the sleeve 65 is pushed toward the needle 57 so as to disengage the needle 57 from the remainder of the syringe 55.

It is foreseen that the needle removing mechanism of the present invention can be utilized with other types of devices used in the medical art for puncturing or penetrating a patient wherein it is important to be able to remove the needle from the mechanism subsequent to patient puncture without touching the needle itself and risking a strike from the needle by the user. For example, the present invention can be utilized with a vacutainer to withdraw blood from a patient. In a vacutainer, a sleeve would simply slide along the outer wall of the vacutainer, as the sleeves of the illustrated embodiment slide along the body of the syringes.

It is to be understood that while certain forms of the present invention have been illustrated and described herein, it is not to be limited to the specific forms or arrangement of parts described and shown.

What is claimed and desired to be secured by Letters Patent is as follows:

1. A syringe for administering injections comprising:
   (a) a barrel having an interior chamber for holding fluid;
   (b) a plunger reciprocably located in said chamber and manipulative by an administer of an injection;
   (c) a needle having an end point in flow communication with one end of said chamber;
   (d) said needle including a projection extending radially outward therefrom; and
   (e) a sleeve slidably mounted on said barrel and including means for engaging said needle projection subsequent to administration of said injection such that an administrator may engage said needle projection with said means by sliding said sleeve along said barrel and subsequently disconnect said needle from said barrel by rotation of said sleeve.

2. The syringe according to claim 1 wherein:
   (a) said sleeve includes an annular portion mounted on said barrel and both slidable along and rotatable with respect to said barrel.

3. The syringe according to claim 2 wherein:
   (a) said sleeve has a needle engaging first end and said means comprises a slot starting at said first end and extending along said sleeve.

4. The syringe according to claim 3 wherein:
   (a) said projection comprises an ear projecting outwardly from a base of said needle.

5. The syringe according to claim 3 wherein:

(a) said slot is a firt slot and said sleeve includes a second slot parallel to said first slot; and
(b) said second slot has a width sufficient to slide over said projection and a depth sufficient to allow said sleeve to selectively slide parallel to the needle to substantially completely cover said needle and thereby protect a user from being stuck by said needle end point.

6. In an apparatus including a barrel having an internal chamber and a needle for penetrating the skin of a patient and allowing fluid to flow between the patient and the chamber and wherein the needle is twist connected to and mounted on the barrel; the improvement comprising:
(a) means slidably mounted radially outward from said barrel so as to be engageable with said needle to allow a user of said apparatus to engage and twist said needle with said means subsequent to use of said needle and thereby remove said needle from said barrel without directly touching said needle.

7. The apparatus according to claim 6 wherein:
(a) said needle being mounted on said barrel with a twist connection; and
(b) said means comprises an annular sleeve both slidable along and rotatable about said barrel having a first needle engaging end; said engaging end for engaging and twisting said needle to disengage said twist connection.

8. A syringe for administration of injections comprising:
(a) an elongate barrel having a central axis and an interior chamber for holding fluid;
(b) a plunger reciprocably positioned in said chamber and being manipulative by an administrator of an injection to allow the plunger to move back and forth within said chamber along the axis of said barrel;
(c) a needle having an end point in flow communication with one end of said chamber opposite said plunger; said needle including a base removably twist connected to said barrel;
(d) a leur lock mechanism for connecting said needle base to said barrel;
(e) a pair of ears extending radially outward from opposite sides of said base and being fixedly connected to said base; and
(f) an annular sleeve mounted on said barrel so as to slide axially along said barrel and to rotate about said barrel; said sleeve having a first needle engaging end and an opposite end; said sleeve first end having a first set of shallow slots and a second set of deep slots starting thereat and extending along said sleeve; said first set of slots being sized and positioned such that when said sleeve is slid along said barrel in alignment with said needle ears, said first set of slots receives said ears so as to allow a user to rotate said ears and consequently said needle by means of rotation of said sleeve; said second set of slots being sized and positioned such as to allow said ears to be received in and slide along said second set of slots, when said sleeve is slid axially along said barrel with said ears aligned with said second set of slots, such that said sleeve extends outwardly over said needle so as to protect a user from being accidentally stuck by said needle end after use of said needle.

9. In an apparatus including a barrel having an internal chamber and a needle for penetrating the skin of a patient and allowing fluid to flow between the patient and the chamber and wherein the needle is twist connected to the barrel; the improvement comprising:
(a) means slidably mounted on said barrel so as to be engageable with said needle to allow a user of said apparatus to engage and twist said needle with said means subsequent to use of said needle and thereby remove said needle from said barrel without directly touching said needle;
(b) said means comprising an annular sleeve both slidable along and rotatable about said barrel having a first needle engaging end;
(c) said needle includes a base having a projection extending radially outward therefrom; and
(d) said sleeve includes a projection engaging slot on said first end thereof.

10. The apparatus according to claim 9 wherein:
(a) said slot is a first slot and said sleeve includes a second slot parallel to said first slot; and
(b) said second slot has a width sufficient to slide over said projection and a depth sufficient to allow said sleeve to selectively slide parallel to said needle to substantially completely cover said needle and thereby protect a user from being stuck by said needle.

* * * * *